United States Patent [19]

Kato

[11] Patent Number: 5,817,521
[45] Date of Patent: Oct. 6, 1998

[54] METHOD FOR DETECTION OF PERFORMANCE REDUCTION OF EXHAUST GAS PURIFICATION CATALYST

[75] Inventor: Nobuhide Kato, Ama-gun, Japan

[73] Assignee: NGK Insulators, Ltd., Japan

[21] Appl. No.: 759,529

[22] Filed: Dec. 5, 1996

[30] Foreign Application Priority Data

Dec. 18, 1995 [JP] Japan .................................. 7-328615

[51] Int. Cl.⁶ .......................... B01J 23/42; B01J 21/08; B01J 29/04; G01N 27/416
[52] U.S. Cl. .......................... 436/151; 502/334; 502/261; 502/262; 502/332; 502/60; 423/213.5; 436/147
[58] Field of Search .................................. 436/151, 147; 502/334, 261–62, 332, 60; 423/213.5

[56] References Cited

U.S. PATENT DOCUMENTS

| | | | |
|---|---|---|---|
| 5,459,997 | 10/1995 | Takemoto et al. | 60/276 |
| 5,497,619 | 3/1996 | Yamada et al. | 60/279 |
| 5,571,763 | 11/1996 | Takemoto et al. | 502/262 |

FOREIGN PATENT DOCUMENTS

| | | |
|---|---|---|
| 264379 | 3/1978 | Germany . |
| 4308894 | 9/1994 | Germany . |
| 62-61919 | 4/1987 | Japan . |
| 63-83415 | 6/1988 | Japan . |
| 2282467 | 4/1995 | United Kingdom . |
| 91/14855 | 10/1991 | WIPO . |
| 93/20340 | 10/1993 | WIPO . |

*Primary Examiner*—Cecilia J. Tsang
*Assistant Examiner*—S. G. Marshall
*Attorney, Agent, or Firm*—Parkhurst & Wendel

[57] ABSTRACT

A method for detecting the performance reduction of an exhaust gas purification catalyst by examining the temperature of an exhaust gas flowing into the catalyst, necessary for the activation of the catalyst. This method enables accurate detection of the performance reduction of an exhaust gas purification catalyst without conducting a constant-speed vehicle operation for a long time.

8 Claims, 3 Drawing Sheets

METHOD FOR DETECTION OF PERFORMANCE REDUCTION OF EXHAUST GAS PURIFICATION CATALYST

BACKGROUND OF THE INVENTION

1. Field Of The Invention

The present invention relates to a method for detection of the performance reduction of an exhaust gas purification catalyst used in automobile or the like.

2. Description Of Related Art

Exhaust gases are discharged from, for example, internal combustion engines, external combustion engines and combustion furnaces all using, as the fuel, a fuel oil, a gas oil, a gasoline, a natural gas or the like, and contain unburnt combustible components (e.g. hydrocarbons, carbon monoxide and hydrogen), nitrogen oxides, etc. In order to oxidize the combustible components and reduce the nitrogen oxides to reduce their contents in exhaust gas, exhaust gas purification catalysts are in wide use particularly in automobiles. Generally known as the exhaust gas purification catalysts are those catalysts containing a noble metal(s) such as platinum, palladium, rhodium or (and) the like.

These exhaust gas purification catalysts, when used for a long period of time, cause performance reduction owing to the scattering or oxidation of noble metal(s) at high temperatures and become incapable of sufficiently oxidize combustible components; as a result, the concentration of combustible components present in the exhaust gas leaving the catalyst increases as compared to that when the catalyst is fresh.

The control for automobile exhaust gas is becoming stricter year by year owing to the increased worldwide recognition for environmental protection in recent years. For example, in California State of U.S., LEVs (low emission vehicles) and ULEVs (ultra low emission vehicles) must light, by the law, a malfunction indicator lamp (MIL) when, during their operation, the amount of hydrocarbons discharged from the engines becomes 1.5 times the maximum hydrocarbon amount set for a new vehicle operating according to the Federal Test Procedure (FTP).

Therefore, it has been necessary to develop a method capable of detecting the performance reduction of an exhaust gas purification catalyst, particularly a method capable of detecting, at a high sensitivity, the performance reduction of an exhaust gas purification catalyst, having a high correlation with the amount of hydrocarbons discharged; and various studies have been made on the method for detection of the performance reduction of catalyst.

For example, Japanese Utility Model Application Kokai (Laid-Open) No. 62-61919 discloses a method for detection of the performance reduction of a catalyst by providing each one temperature sensor upstream and downstream of the catalyst and comparing the temperatures of exhaust gases upstream and downstream of the catalyst. This method utilizes a phenomenon that, when the catalyst shows performance reduction; the temperature of exhaust gas downstream of the catalyst decreases because the oxidation reaction of combustible components catalyzed by the catalyst is an exothermic reaction.

Japanese Utility Model Application Kokai (LaidOpen) No. 63-83415 discloses a method for detection of the performance reduction of a catalyst by providing an oxygen sensor downstream of the catalyst and analyzing the signal wave form given by the sensor. This method utilizes a phenomenon that the performance reduction of catalyst tends to reduce the oxygen adsorbability of the catalyst.

In the method for detection of the heat amount generated by the catalytic reaction, however, the difference in exhaust gas temperature between upstream and downstream of the catalyst, brought about by the exothermic reaction can be detected only after the automobile provided with the catalyst has been operated for several minutes at a constant speed of 40–60 km/h to stabilize the exhaust gas system thermally, because the catalyst has a large heat capacity. Moreover, in the method, in order to detect the performance reduction of catalyst at a higher accuracy, longer-time operation at the above constant speed is necessary.

The operation under the above conditions is practically impossible in actual running where acceleration and deceleration are repeated, and the accurate detection of the performance reduction of catalyst by the above method is almost impossible.

In the method for detection of the oxygen adsorbability of catalyst, there are cases when the catalyst shows no reduction in oxygen adsorbability; therefore, the method has a problem in accuracy.

OBJECT AND SUMMARY OF THE INVENTION

The present invention has been made in view of the above situation. The object of the present invention is to provide a method for detection of the performance reduction of an exhaust gas purification catalyst, which can detect the performance reduction of the catalyst accurately without conducting constant-speed vehicle running for a long time.

According to the present invention, there is provided a method for detection of the performance reduction of an exhaust gas purification catalyst, which comprises; providing the exhaust gas purification catalyst which is activated with the temperature increase of an exhaust gas flowing thereinto and thereby reduces the concentrations of combustible components and nitrogen oxides contained in the exhaust gas, and detecting an increase in the activation temperature of the catalyst.

In the present invention, it is preferable that the increase in the activation temperature of the catalyst is detected by detecting an increase in the temperature of an exhaust gas flowing into the catalyst, necessary for the activation of the catalyst. In the present invention, it is also preferable that the activation of the catalyst is detected by examining that the difference between the temperature of an exhaust gas flowing into the catalyst and the temperature of an exhaust gas leaving the catalyst has reached a predetermined level. In the present invention, it is also preferable that the predetermined level of the above difference is −50° C. to 200° C.

According to the present invention, there is further provided a method for detection of the performance reduction of an exhaust gas system which comprises; providing the exhaust gas system comprising at least one exhaust gas purification catalyst which is activated with the temperature increase of an exhaust gas flowing thereinto and thereby reduces the concentrations of combustible components and nitrogen oxides contained in the exhaust gas, and detecting an increase in the activation temperature of the most upstream exhaust gas purification of the system.

BRIEF DESCRIPTIONS OF THE DRAWINGS

DETAILED DESCRIPTION OF THE INVENTION

Figure 1:
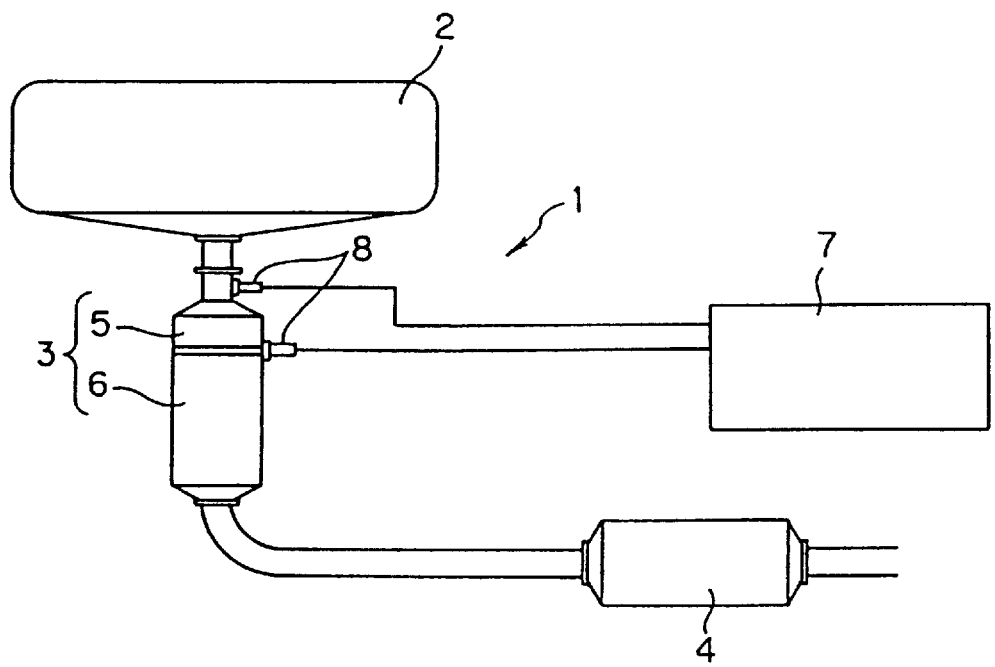
FIG. 1 is a schematic drawing showing an exhaust gas system of automobile engine.

In the present invention, the performance reduction of an exhaust gas purification catalyst is detected by detecting an increase in the temperature of the catalyst necessary for its activation, i.e. the activation temperature of the catalyst. For the activation of an exhaust gas purification catalyst, it is necessary to heat the catalyst up to a particular temperature, i.e. its activation temperature. When the temperature of the catalyst is lower than the activation temperature, the catalyst shows no catalysis. This activation temperature, when the catalyst shows a reduced performance, increases because the oxidizing ability of the noble metal supported on the catalyst decreases. Therefore, the performance reduction of an exhaust gas purification catalyst can be detected by detecting an increase in the activation temperature of the catalyst.

The activation temperature may be represented, for example, by a $T_c$ (a catalyst temperature measured) when $(T_c-T_{in})$ ($T_{in}$ is a temperature of an exhaust gas entering the catalyst) has reached a predetermined level, or by a $T_{c'}$[a catalyst temperature calculated from $T_{in}$ (a temperature of an exhaust gas entering the catalyst) and $T_{out}$ (a temperature of an exhaust gas leaving the catalyst)] when $(T_{c'}-T_{in})$ has reached a predetermined level. However, the activation temperature is represented preferably by a $T_{in}$ (a temperature of an exhaust gas entering the catalyst) when $(T_c-T_{in})$ or $(T_{c'}-T_{in})$ has reached a predetermined level, i.e. when the catalyst has been activated. This is because while measurement of catalyst temperature $T_c$ tends to give scattered values depending upon, for example, the fixation position of temperature sensor or thermocouple, measurement of exhaust gas temperature tends to give far less scattered values and is stable.

Incidentally, there may be taken, as $T_{c'}$, an average value calculated from $T_{in}$ and $T_{out}$ when the catalyst-inside temperature is simply assumed to have a linear distribution, i.e. $(T_{in}+T_{out})/2$; or an average value determined from $T_{in}$ and $T_{out}$ when the catalyst-inside temperature is assumed to have an exponential distribution; or a value obtained experimentally beforehand from $T_{in}$ and $T_{out}$. Also, $T_c$ may be represented by $T_{out}$.

An exhaust gas purification catalyst is generally activated with an increase in the temperature of an exhaust gas flowing thereinto from an internal combustion engine or the like. Therefore, the temperature of an exhaust gas necessary for catalyst activation increases as the performance of the catalyst is reduced. Hence, an increase in the activation temperature of catalyst, i.e. the performance reduction of catalyst can be detected indirectly by detecting an increase in the exhaust gas temperature necessary for catalyst activation.

In detecting the performance reduction of a catalyst specifically, there are examined, in advance, the exhaust gas temperature for catalyst activation, corresponding to the allowable upper limit of hydrocarbon concentration in exhaust gas leaving the catalyst; the current level of the exhaust gas temperature is measured; and, when the level reaches the above value examined in advance, the catalyst is judged to have a reduction in performance.

When the catalyst has a large heat capacity, the temperature change of an exhaust gas flowing thereinto is quick as compared with the temperature change of the catalyst. During the deceleration of engine speed, the temperature of an exhaust gas flowing into the catalyst decreases although the catalyst is not activated, and $(T_c-T_{in})$ shows an apparent value higher than the predetermined level. In such a case, the temperature $(T_{in})$ of an exhaust gas flowing into the catalyst may be represented by an average value during a predetermined length of time determined from the heat capacity of catalyst experimentally or by calculation. Alternatively, $T_{in}$ may be obtained by determining a time lag of increase in catalyst temperature beforehand experimentally or by calculation and measuring the temperature of an exhaust gas flowing into the catalyst, at a timing earlier by the time lag.

The present invention method enables rapid and easy detection of the performance reduction of an exhaust gas purification catalyst without conducting constant-speed vehicle running for a long time. Further, since there is a high correlation between (1) increase in activation temperature and (2) hydrocarbon concentration in exhaust gas, the present invention method enables accurate detection of the performance reduction of catalyst and, moreover, can examine the conformity of a vehicle to the above-mentioned hydrocarbon control set by California State, U.S. for operation according to the FTP.

In the present invention, it is preferable that the activation of the catalyst is confirmed by examining that the difference between the temperature of an exhaust gas flowing into the catalyst and the temperature of an exhaust gas leaving the catalyst has reached a predetermined level.

As mentioned above, the oxidation reaction of combustible components catalyzed by an exhaust gas purification catalyst is an exothermic reaction. Therefore, when the catalyst has been activated, the temperature of an exhaust gas leaving the catalyst is higher than the temperature of an exhaust gas entering the catalyst. Thus, the activation of a catalyst can be confirmed by measuring the difference between the temperature of an exhaust gas leaving the catalyst and the temperature of an exhaust gas entering the catalyst.

The temperature difference (between the temperature of an exhaust gas entering the catalyst and the temperature of an exhaust gas leaving the catalyst) adequately used for the detection of catalyst activation, is preferably −50° C. to 200° C., more preferably 0 to 100° C. in consideration of the factor that the temperature of exhaust gas is decreased by the temperature increase of catalyst.

Figure 6:
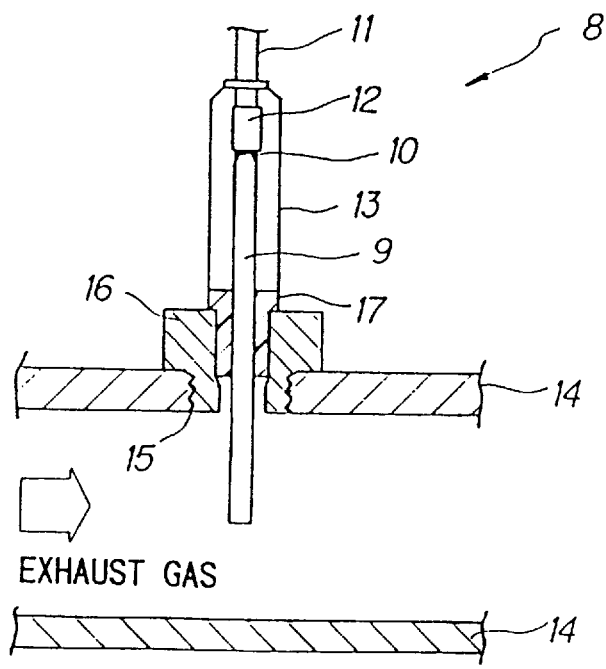
FIG. 6 is a schematic sectional view showing an example of the temperature sensor used in the method of the present invention.

In the present invention, measurement of temperature is conducted by the use of a temperature sensor, a thermocouple or the like. Temperature measurement by a temperature sensor is preferred. As the temperature sensor, there is used, for example, one shown in FIG. 6. In FIG. 6, the temperature sensor 8 is covered with a ceramic material and comprises a resistor 9 containing a metal having a positive temperature coefficient of resistance, a potentiometric resistance 10 connected to one end of the resistor 9, a connector 12 connecting the potentiometric resistance 10 and a line 11, and a casing 13 accommodating one end of the resistor 9, the potentiometric resistance 10, the connector 12 and one end of the line 11. This temperature sensor 8 measures the temperature of exhaust gas by utilizing a fact that the resistance of the resistor 9 changes in accordance with the change of the temperature, and is used by inserting one end of the resistor 9 projecting from the casing 13, into an exhaust pipe 14 through a hole 15 made in the wall of the exhaust pipe 14. The fixation of the resistor 9 to the hole 15 is conducted via a housing 16 having a portion engaged with the hole 15. A buffer material 17 is used between the housing 16 and the resistor 9. One end of the resistor 9 positioned inside the exhaust pipe may be covered with a protective material.

An exhaust gas system is ordinarily constituted by connecting a plurality of exhaust gas purification catalysts to an internal combustion engine or the like. When the performance reduction of such an exhaust gas system is required to be detected, detection of the performance reduction of the most upstream exhaust gas purification catalyst is sufficient when the internal combustion engine side of the exhaust gas system is regarded as the upstream side thereof. This is because (1) hydrocarbons are generated only at the initial period of engine start, (2) the plurality of catalysts reach their activation temperatures in the order of the most upstream catalyst, the next upstream catalyst, . . . and (3) the most part of hydrocarbons is treated by the most upstream catalyst.

The present invention is hereinafter described by way of Example. However, the present invention is not restricted to the Example.

Using the above-mentioned method of the present invention, the performance reduction of exhaust gas purification catalyst was detected and the hydrocarbon concentration in exhaust gas leaving the catalyst was examined.

In FIG. 1 is shown the exhaust gas system used in the present Example. The exhaust gas system 1 of FIG. 1 comprises a 2.0 liter in-line four-cylinder engine 2, a light-off catalyst 3 provided downstream of the engine 2, and a 1,700 cc main catalyst 4 provided downstream of the light-off catalyst 3. The light-off catalyst 3 is divided into a 200 cc upstream light-off catalyst 5 and a 1,200 cc downstream light-off catalyst 6. Each one temperature sensor 8 is provided in exhaust pipes positioned upstream and downstream of the upstream light-off catalyst 5. The outputs of the temperature sensors 8 are sent to a device 7 for measurement, control and calculation.

The exhaust gas generated in the engine 2 passes through the light-off catalyst 3 (the upstream light-off catalyst 5 and the downstream light-off catalyst 6) and is discharged. The device 7 for measurement, control and calculation reads the signals sent from the temperature sensors 8, calculates the exhaust gas temperature for activation and, depending upon the resulting data, issues a signal for lighting of MIL or the like.

As the upstream light-off catalyst 5, there were prepared three kinds, i.e. a fresh catalyst (showing no performance reduction), a catalyst subjected to aging of 750° C. ×100 hours, and a catalyst subjected to aging of 850° C.×100 hours. As the downstream light-off catalyst 6, there were prepared two kinds, i.e. a fresh catalyst (showing no performance reduction) and a catalyst subjected to aging of 850° C.×100 hours. As the main catalyst 4, there was prepared a fresh catalyst (showing no performance reduction).

By appropriately combining the above three kinds of catalysts, three kinds of exhaust gas systems shown in Table 1 were prepared.

TABLE 1

| Exhaust gas system | Upstream light-off catalyst | Downstream light-off catalyst | Main catalyst |
| --- | --- | --- | --- |
| A | Fresh | Fresh | Fresh |
| B | Aging of 750° C. × 100 hours | Aging of 850° C. × 100 hours | Fresh |
| C | Aging of 850° C. × 100 hours | Aging of 850° C. × 100 hours | Fresh |

Each of the three kinds of exhaust gas systems shown in Table 1 was mounted on an automobile, and measured for the hydrocarbon amount discharged during running in the FTP mode. The results are shown in Table 2.

TABLE 2

| Exhaust gas system | Hydrocarbon amount discharged (g/mile) |
| --- | --- |
| A | 0.037 |
| B | 0.040 |
| C | 0.046 |

Figure 2:
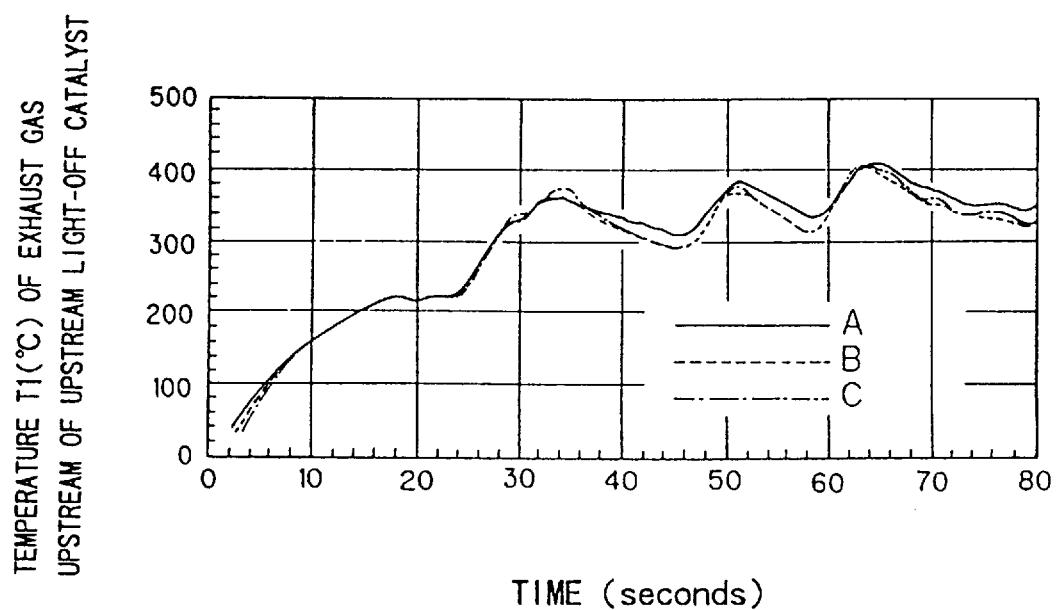
FIG. 2 is a graph showing a change with time, of the temperature (T1) at a position upstream of the upstream light-off catalyst of the exhaust gas system of FIG. 1.
Figure 3:
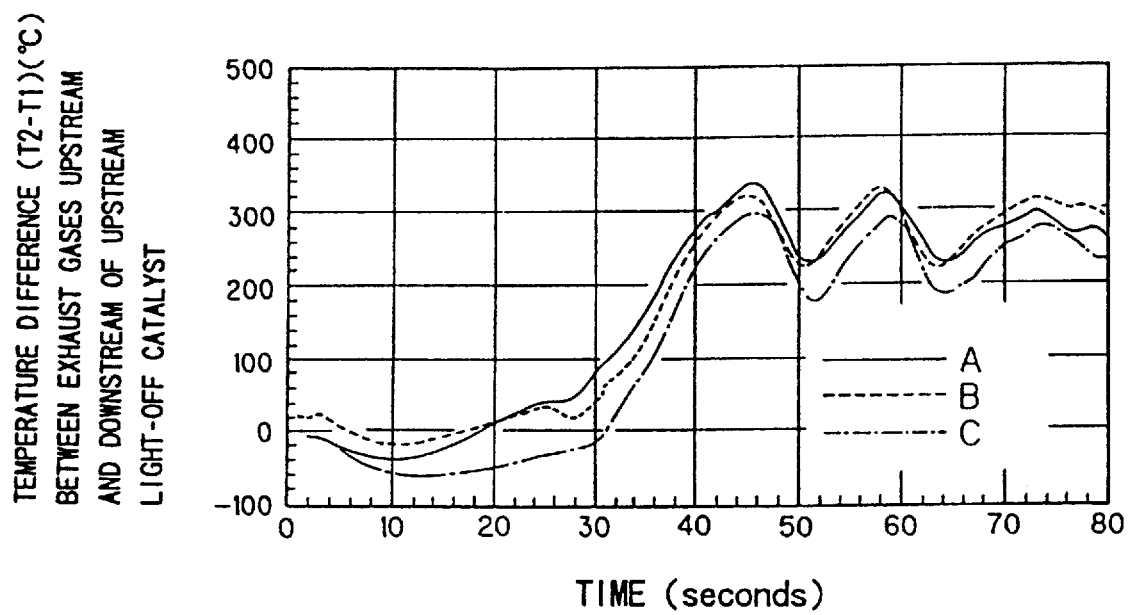
FIG. 3 is a graph showing a change with time, of the temperature difference (T2-T1) between positions upstream and downstream of the upstream light-off catalyst of the exhaust gas system of FIG. 1.
Figure 4:
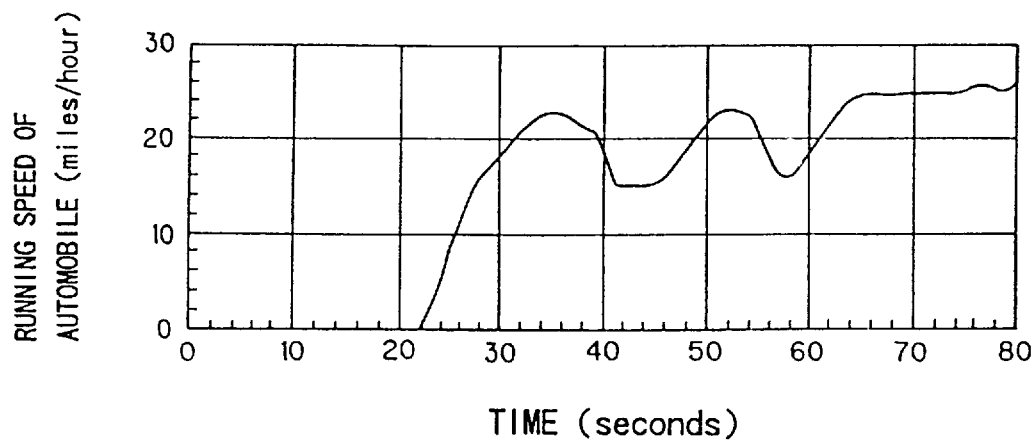
FIG. 4 is a graph showing a change with time, of the running speed of automobile.

By using the temperature sensors 8, the exhaust gases upstream and downstream of the upstream light-off catalyst 5 were measured for the temperatures for 80 seconds after the start of engine, on each of the exhaust gas systems A, B and C. In FIG. 2 is shown a change with time, of the temperature (T1) of exhaust gas upstream of the upstream light-off catalyst 5. In FIG. 3 is shown a change with time, of the temperature difference (T2-T1) between the temperature (T2) of exhaust gas downstream of the upstream light-off catalyst 5 and the temperature (T1) of exhaust gas upstream of the upstream light-off catalyst 5. In FIG. 4 is shown a change with time, of the running speed of automobile. Incidentally, the negative value of (T2-T1) in FIG. 3 indicates that the temperature (T2) of exhaust gas downstream of the catalyst 5 was lower than the temperature (T1) of exhaust gas upstream of the catalyst 5; and the positive value of (T2-T1) indicates that an exothermic reaction took place owing to the activation of the catalyst 5 and that the temperature of exhaust gas downstream of the catalyst 5 increased.

Figure 5:
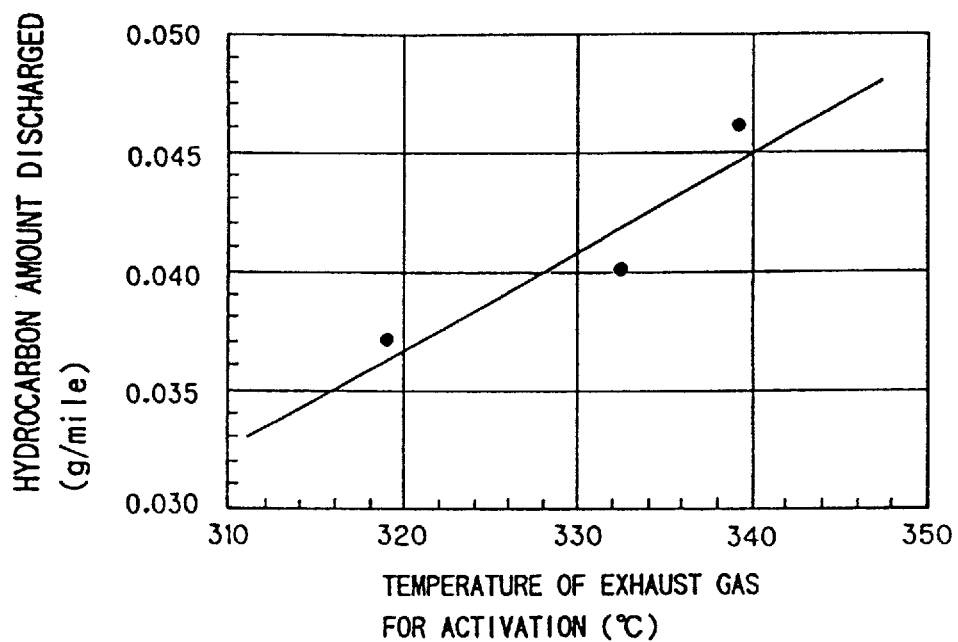
FIG. 5 is a graph showing a correlation between the exhaust gas temperature for catalyst activation and the hydrocarbon amount discharged.

In FIG. 5 is shown a relation between the exhaust gas temperature for activation and the hydrocarbon amount discharged, when (T2-T1) has reached 50° C. (at this temperature difference, the catalyst is judged to have been activated). The coefficient $R^2$ of correlation between the exhaust gas temperature for activation and the hydrocarbon amount discharged is 0.861 and the correlation between them is high.

The hydrocarbon limit for new ULEV in FTP running is 0.04 g/mile. The exhaust gas temperature for activation when the hydrocarbon amount discharged has reached 1.5 times the above hydrocarbon limit, i.e. 0.06 g/mile, can be obtained from FIG. 5. Thus, a malfunction indicator lamp (MIL) can be lighted when the exhaust gas temperature for activation, of a vehicle has reached the value obtained above from FIG. 5.

In the present invention, the performance reduction of an exhaust gas purification catalyst can be known from the exhaust gas temperature necessary for activation of the catalyst. Therefore, the present method enables rapid, easy and accurate detection of the performance reduction of an exhaust gas purification catalyst without conducting a constant-speed vehicle operation of long time. Further, the present method for detection of the performance reduction of an exhaust gas purification catalyst can examine the conformity of a vehicle to the above-mentioned hydrocarbon control set by California State, U.S. for FTP running.

What is claimed is:

1. A method for detection of the performance reduction of an exhaust gas purification catalyst, which comprises;

providing the exhaust gas purification catalyst which is activated with the temperature increase of an exhaust gas flowing thereinto and thereby reduces the concentrations of combustible components and nitrogen oxides contained in the exhaust gas, and detecting an increase in the activation temperature of the catalyst.

2. A detection method according to claim 1, wherein the increase in the activation temperature of the catalyst is detected by detecting an increase in the temperature of an exhaust gas flowing into the catalyst, necessary for the activation of the catalyst.

3. A detection method according to claim 2, wherein the activation of the catalyst is detected by examining that the difference between the temperature of an exhaust gas flowing into the catalyst and the temperature of an exhaust gas leaving the catalyst has reached a predetermined level.

4. A detection method according to claim 3, wherein the predetermined level is −50° C. to 200° C.

5. A method for detection of the performance reduction of an exhaust gas system which comprises;

providing the exhaust gas system comprising at least one exhaust gas purification catalyst which is activated with the temperature increase of an exhaust gas flowing thereinto and thereby reduces the concentrations of combustible components and nitrogen oxides contained in the exhaust gas, and detecting an increase in the activation temperature of the most upstream exhaust gas purification of the system.

6. A detection method according to claim 5, wherein the increase in the activation temperature of the catalyst is detected by detecting an increase in the temperature of an exhaust gas flowing into the catalyst, necessary for the activation of the catalyst.

7. A detection method according to claim 6, wherein the activation of the catalyst is detected by examining that the difference between the temperature of an exhaust gas flowing into the catalyst and the temperature of an exhaust gas leaving the catalyst has reached a predetermined level.

8. A detection method according to claim 7, wherein the predetermined level is −50° C. to 200° C.

* * * * *